United States Patent [19]

Özdamar et al.

[11] Patent Number: 5,230,344
[45] Date of Patent: Jul. 27, 1993

[54] EVOKED POTENTIAL PROCESSING SYSTEM WITH SPECTRAL AVERAGING, ADAPTIVE AVERAGING, TWO DIMENSIONAL FILTERS, ELECTRODE CONFIGURATION AND METHOD THEREFOR

[75] Inventors: Özcan Özdamar; Rafael E. Delgado, both of Miami, Fla.

[73] Assignee: Intelligent Hearing Systems Corp., Miami, Fla.

[21] Appl. No.: 924,678

[22] Filed: Jul. 31, 1992

[51] Int. Cl.$^5$ ............................................. A61B 5/04
[52] U.S. Cl. ................................. 128/731; 128/746
[58] Field of Search ............... 128/731, 732, 745, 746; 364/413.02

[56] References Cited

U.S. PATENT DOCUMENTS

| | | | |
|---|---|---|---|
| 4,592,087 | 5/1986 | Killon | 381/68 |
| 4,689,819 | 8/1987 | Killon | 381/68 |
| 4,846,190 | 7/1989 | John | 128/731 |
| 4,987,903 | 1/1991 | Keppel et al. | 128/731 |
| 5,099,856 | 3/1992 | Killon | 128/731 |

OTHER PUBLICATIONS

Don et al. Objetive Detection of Averaged Auditory Brainstem Responses, Scand Audiology, vol. 13, pp. 219-228, 1984.
Elberling et al. Quality Estimation of Averaged Auditory Brainstem Responses, Scan Audiology, vol. 13, pp. 187-197, 1984.
Mocks et al. Variability of Single Visual Evoked Potentials Evaluated by Two New Statistical Tests, Electroencephalography and Clinical Neurophysiology, vol. 57, pp. 571-580 1984.
Turetsky et al. Noise and Signal Power and their Effects on Evoked Potential Estimation, Electroencephalography and Clinical Neurophysiology, vol. 71, pp. 310-318, 1988.
Digital Image Processing by R. Gonzalez et al. pp. 72-79, 1987.
Sgro et al. Real-Time Reconstruction of Evoked Potentials Using a New Two-Dimensional Filter Method, Electroencephalography and Clinical Neurophysiology, vol. 62, pp. 372-380, 1985.
IHS product brochure for OPTI-AMP, 1990.
IHS product brochure for SMART-EP, 1990 discloses standard averaging system.
Grass Instrument Co. product brochure for GRASS Model P511 amplifier, 1985.
Spectrum Signal Processing product brochure for TM S320C25 processor board, 1992.

Primary Examiner—Kyle L. Howell
Assistant Examiner—George Manuel
Attorney, Agent, or Firm—Robert C. Kain, Jr.

[57] ABSTRACT

The evoked potential processing system includes, in one embodiment, a spectral averaging method. Time based, digital pre-stimulus and post-stimulus electroencephalographic (EEG) signal streams are obtained and are converted into frequency spectrum signals. A differential spectrum is obtained. The differential spectrums from a plurality of sweeps are summed. The summed differential spectrum is then converted into a time based signal stream which contains the evoked potential (EP) signal therein. The EP signal can also be obtained utilizing a two-dimensional filter. Pre- and post-stimulus EEG signal streams for a sub-group of stimuli, wherein each stimulus in a group has the same intensity or frequency, are filtered by conventional averaging or spectral differential averaging. The time based, filtered, post-stimulus EEG signal streams are placed in an array and the array is then filtered by a two-dimensional Fast Fourier Transform (FFT) filter. The array is then filtered by a mask and the masked array is then transformed into a time based format by an inverse FFT. The adaptive averaging technique utilizes a computational formula which computes an estimated running signal to noise ratio. When the difference between the pre-stimulus running SNR and the post-stimulus running SNR is less than a predetermined threshold, further stimulation and acquisition of EEG signals stops. Hence, the post-acquisition processing of the EEG signals is limited to that number of EEG sweeps. The electrode wire configuration uses a cross wiring scheme wherein the shield of a particular wire is connected to the other electrode wire to eliminate artifacts in the respective electrode wire.

26 Claims, 12 Drawing Sheets

FIG. 12
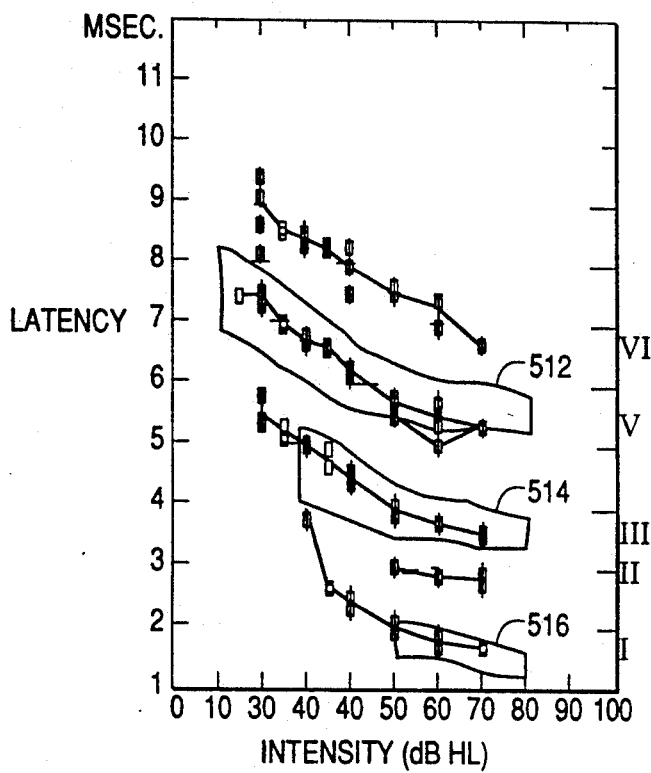
FIG. 13
FILE: A:jwLALAT. DAT
THRESHOLD RESPONSE:
INTENSITY : 15dB HL
LATENCY : 7.43 MSEC.
INTERPEAK INTERVALS:
PEAKS I-III : 1.92 MSEC.
PEAKS III-V: 1.77 MSEC.
PEAKS I-V : 3.69 MSEC.
STIM: CLICK
FREQ. : _____
FIG. 14
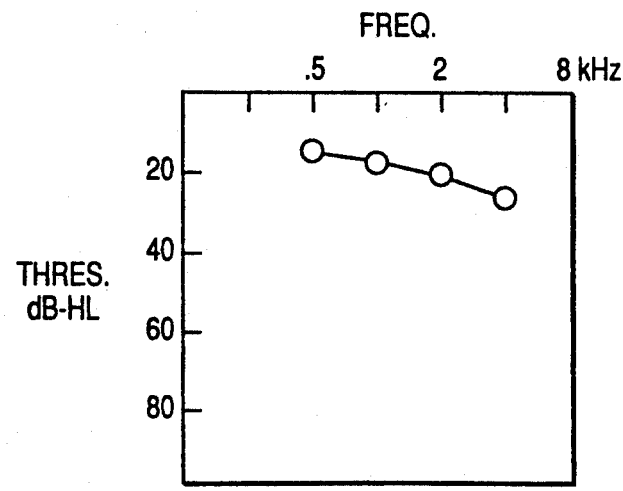

EVOKED POTENTIAL PROCESSING SYSTEM WITH SPECTRAL AVERAGING, ADAPTIVE AVERAGING, TWO DIMENSIONAL FILTERS, ELECTRODE CONFIGURATION AND METHOD THEREFOR

BACKGROUND OF THE INVENTION

The present invention relates to an evoked potential processing system. The processing system includes special processing methods such as spectral averaging, variable sweep averaging or adaptive averaging, two-dimensional filtering, and/or a special electrode wire configuration.

The brain wave activity of a patient or a living being may be monitored by sensing electroencephalographic (EEG) signals sensed on the skull of the patient or living being. Essentially, electrodes are placed on the skull in order to sense EEG activity. The response of a brain to stimulus is indicative of the condition of the subject. For example, auditory brain stem response can be used as a tool to assess the auditory function in certain patients, particularly infants. EP signals can also be used to detect the subject's condition during surgery. Auditory brain stem response (ABR) reveals information regarding the peripheral organ, that is, the ear, and the brain stem auditory pathways. Since ABR is non-invasive and does not require anesthesia or sedation, such tests can be easily administered in office environments or in new born nurseries. In some instances, ABR measurements are obtained utilizing auditory clicks wherein each click has a certain pulse width, a certain intensity or amplitude level and covers a broad frequency band. Alternatively, an ABR measurement can utilize frequency specific audio stimuli such as tone bursts for special testing paradigms or test patterns.

Rather than use audio stimuli to affect EEG activity, visual stimuli could be used. Flashes of light (broad band frequency spectrum), intensity specific visual stimuli, hue or color stimuli, frequency specific stimuli and checkerboard pattern visual stimuli could be used. Further, somato sensory stimuli could be utilized, such as tactile or physical stimulus or electrical pulse stimulus. These types of stimuli affect EEG activity and such stimuli can be used to test brain stem pathways and peripheral sensory activity.

Auditory brain stem response (ABR) tests using click evoked ABR thresholds have been quite effective in determining average hearing sensitivity in the mid frequency (2-4 kHz) range. However, these click evoked ABRs give little information about the shape of an audiogram. Latency, the time delay of certain waveform shapes in the EEG signal stream obtained during an ABR test, are considered better estimates of the audiogram. These estimates of the audiogram can be used to generate a family of audiograms since there can be more than one audiogram producing the same latency-intensity functions.

Rapid acquisition of evoked potentials can be achieved primarily by three approaches: a) employing signal enhancement processing methods, b) using high stimulus rates, and c) testing both ears simultaneously. The first approach requires an innovative process other than the traditional averaging. Traditional averaging normally involves stimulating EEG activity with multiple, timed stimuli, obtaining the time based EEG signal streams with a time base reference link to the application of the stimulus, adding and averaging coincidental time segment EEG signals, both pre-stimulus and post-stimulus EEG signals. Limitations of the traditional ensemble averaging method in evoked potential acquisition have long been recognized. The problem arises primarily from the poor signal to noise ration (SNR), the nonstationary nature of the noise (that is, the noise may move with time) and the small amplitude of the signal response.

The second approach to speed up the EP acquisition process requires the increase of the stimulus repetition rate. This, however, generally changes the physiological characteristics of the system reducing the usefulness of the responses. Typically, at high stimulus rates neural adaptation takes place and responses are reduced and prolonged. This effect, however, can be reduced or eliminated by taking advantage of the special characteristics of the sensory organ. For the auditory system, intensity and frequency of tonal stimuli can be ordered such that adaptation is kept at a minimum.

A third approach is to use techniques that will allow the simultaneous recording from both ears thus effectively halving the testing time for each ear. Recordings from concurrent presentation of slightly different rate sound stimuli to both ears can be averaged and evoked potentials, EPs, can be separately obtained.

Automated response detection techniques can be broadly classified in two groups: EP signal statistic-based methods and EP waveform-based methods. Statistic-based methods compute various statistical measures of individual and average responses across time and sequences to detect the presence of a response. $F_{sp}$ is a statistical approach using variance analysis in calculating the ratio of the ABR to the estimated averaged background noise. See the article entitled "Objective Detection of Averaged Auditory Brainstem Responses" by M. Don, et al. and the article entitled "Quality Estimation of Average Auditory Brainstem Responses" by C. Elberling, et. al. Waveform-based methods detect the presence of a response by comparing the test waveform to another waveform either learned previously by the system or acquired under similar or no-stimulus conditions.

While the response recognition problem has been given adequate attention, threshold determination procedures have not received similar attention. This may be due to the fact that under laboratory conditions in which response artifacts are minimal, threshold determination reduces to the trivial problem of level detection.

With current prior art devices, the recording time necessary to determine the ABR threshold for a given stimulus is about 20 minutes (10 recordings, 1024 sweeps). If a four-frequency audiogram is desired, about 80 minutes of recording time are required. For two ears the testing time approaches three hours.

Most processing techniques are configured to obtain a predetermined number of post-stimulus EEG or raw EP signal during the averaging routine. The predetermined number of EEG signals are summed such that substantially identical time based signal segments, referenced to the application of the stimulus for that particular signal sweep, are added together. In order to improve the signal to noise ratio, it is generally thought that the number of signals averaged, n, should be increased. It has been proposed that an SNR value can be estimated using different formulas proposed by various researchers (Möcks et al., 1984; Turetsky et al., 1988).

Also, the use of unbiased estimators has been proposed by Möcks et al.

Where:
SNR = Running signal to noise ratio estimate
$P_s$ = Average signal power
$P_n$ = Average noise power
$X_k(t) = k^{the}$ EEG sweep
K = number of sweeps averaged
T = number of data points in each sweep.

$$S\hat{N}R = \frac{\hat{P}_s}{\hat{P}_n} \qquad \text{Eq. A}$$

$$\hat{P}_s = \frac{1}{T} \sum_{t=1}^{T} \bar{x}_k(t)^2 - \hat{P}_n \qquad \text{Eq. B}$$

$$\hat{P}_n = \frac{1}{T(K-1)} \sum_{t=1}^{T} \sum_{k=1}^{K} [x_k(t) - \bar{x}_k(t)]^2 \qquad \text{Eq. C}$$

As the equations are formulated, it is extremely difficult to compute SNR in real-time with a running average. In addition to requiring many computations, all the single responses must be kept in memory. The computations take longer and longer as the number of averaged sweeps increases. The prior art references did not take into account both pre-stimulus and post-stimulus EEG signals but dealt with only post-stimulus EEG signals.

In addition to being averaged by traditional summation techniques, the EEG signal streams may be filtered with a two-dimensional filter. Two-dimensional filtering is based on the idea that image processing methods can reveal prominent events in an array of consecutive EPs and suppress transient artifacts which occur in individual recordings only. Two-dimensional filtering follows the general principles of image processing which are well known and commonly applied to pictorial type problems (Gonzales & Wintz, 1987). However, evoked potential or EP signals are not normally recognized as including identifiable images or pictures. Accordingly, such multi-dimensional signal processing techniques are seldom used in processing bioelectric signals. Sgro et al. (1985) first proposed two-dimensional filtering for EP reconstruction to track dynamic changes. Sgro's paper discloses the use of a two-dimensional Fast Fourier Transform (FFT) filter to process multiple, EP or EEG signal streams. However, the stimuli used to develop the EP signals were uniform, that is, the intensity and frequency (either click or tone burst) of each stimulus was substantially identical. Sgro first transformed the EP signals using a two-dimensional FFT, then used a mask to drop certain frequencies from the transformed two-dimensional array (those frequencies which exceeded certain pre-determined limits) and then retransformed the array with an inverse FFT to obtain filtered, EP signal streams in the time domain.

OBJECTS OF THE INVENTION

It is an object of the present invention to provide a system and a method for extracting evoked potential signals from a stream of pre- and post-stimulus EEG signals.

It is another object of the present invention to provide a system which generates certain information such as one or more audiograms or one or more latency-intensity curves during an auditory brain stem response in about 5–10 minutes per ear.

It is a further object of the present invention to remove artifacts from EP-EEG signal stream in real time.

It is another object of the present invention to utilize a variable sweep averaging or adaptive averaging using a computational formula to estimate the running signal to noise ratio requiring the storage of the running sum of the time base EEG signal and the square of that running sum.

It is another object of the present invention to utilize a spectral enhancement averaging technique to remove or reduce noise in the EP signals.

It is an additional object of the present invention to utilize a two-dimensional filter to remove noise from the EEG signal streams particularly when the chain of stimuli has increasing levels of intensity and/or frequency.

It is a further object of the present invention to remove artifacts and noise from the EEG evoked potential signals by combining the spectral enhancement averaging and the two-dimensional filter and, hence, identify the evoked potential (EP) signals in the EEG signal streams.

It is an additional object of the present invention to provide an electrode wiring configuration which reduces or eliminates artifacts in the EEG signal carried by the electrode wiring.

SUMMARY OF THE INVENTION

The evoked potential processing system includes, in one embodiment, a spectral averaging method. Time based, digital pre-stimulus and post-stimulus electroencephalographic (EEG) signal streams are obtained and are converted into pre- and post-stimulus frequency spectrum signal streams. A differential spectrum is obtained from each pre- and post-stimulus signal. The differential spectrums from a plurality of sweeps are summed by correlating respective time bases in each differential spectrum and summing coincidental time segments together. The summed differential spectrum is then converted into a time based signal stream which contains the evoked potential (EP) signal therein. The raw EP signal can also be processed utilizing a two-dimensional filter. Pre- and post-stimulus EEG signal streams for a sub-group of stimuli, wherein each stimulus in a group has the same intensity or frequency, are filtered by conventional averaging or spectral differential averaging. The time based, filtered, post-stimulus EEG signal streams are placed in an array and the array is then filtered by a two-dimensional Fast Fourier Transform (FFT) filter. The masked array is then transformed into a time based format by an inverse FFT. The adaptive averaging technique utilizes a computational formula which computes an estimated running signal to noise ratio for the pre- and post-stimulus EEG signal by storing the running sum of a time base segment of each signal stream as well as the square of the time base segment. When the difference between the pre-stimulus running SNR and the post-stimulus running SNR is less than a predetermined threshold, further stimulation and acquisition of EEG signals stops. Hence, the post-acquisition processing of the EEG signals is limited to that number of EEG sweeps. The electrode wire configuration uses a cross wiring scheme wherein the shield of a particular wire is connected to the other electrode wire to eliminate artifacts in the respective electrode wire.

BRIEF DESCRIPTION OF DRAWINGS

Further objects and advantages of the present invention can be found in the detailed description of the preferred embodiments when taken in conjunction with the accompanying drawings in which:

FIG. 12 diagrammatically illustrates latency-intensity curves and ranges therefor;

FIG. 13 diagrammatically illustrates a data information screen;

FIG. 14 diagrammatically illustrates an audiogram;

DETAILED DESCRIPTION OF THE PREFERRED EMBODIMENTS

The present invention relates to an evoked potential (EP) signal processing system using spectral enhancement averaging as one type of processing method, adaptive averaging as another processing method, a two-dimensional filter as a further processing method, and a special electrode wire configuration to eliminate or reduce noise or artifacts in the electrode pick up wiring.

Figure 1:
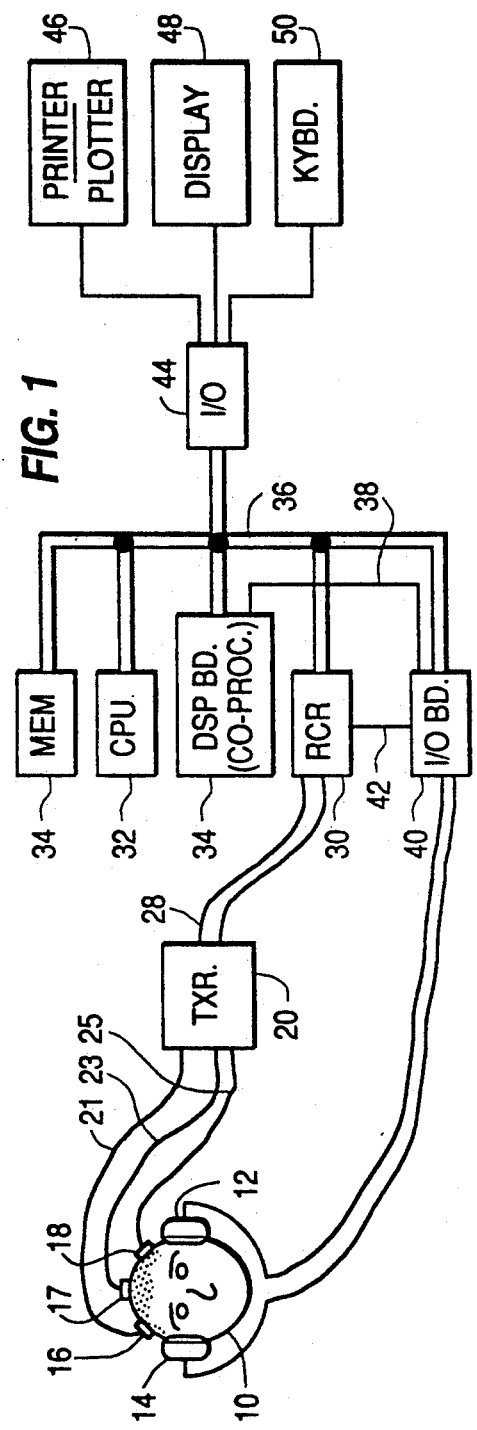
FIG. 1 diagrammatically illustrates a block diagram of the evoked potential system.

FIG. 1 diagrammatically illustrates a block diagram of the system. In the illustrated embodiment, a living being or person 10 is stimulated by headphones 12 and 14 which emit audio clicks or audio tone bursts having a certain intensity or frequecy as generated by the system controls. Audio clicks provide a stimulus spanning a wide range of frequencies. The clicks or tone bursts have a certain pulse width. In one embodiment, 512 stimuli are delivered to headphones 12, 14. There is about a 15 millisecond time period between each stimulus.

A number of electrodes 16, 17 and 18 are attached to the skull of person 10. These electrodes are connected to a transmitter unit 20 which includes a number of bioamplifiers therein. As discussed later, electrode wires 21, 23 and 25 may be configured in a special manner in order to reduce noise in EEG signal carried therein.

Transmitter 20 includes a number of bioamplifiers which are electrically coupled to the electrodes. One transmitter is sold under the trademark OPTI-AMP by Intelligent Hearing Systems of Miami, Fla. The OPTI-AMP includes bioamplifiers for the acquisition of auditory brain stem responses (ABR) and middle latency responses (MLR) and other evoked potential or EEG acquisition systems. Output signals from the OPTI-AMP are fed through optical cables 28 to a receiver in a personal computer. The OPTI-AMP transmitter 20 is placed near the patient such that electrode wires 21, 23, 25 have a relatively short length. The OPTI-AMP transmitter can be configured as either a single or a dual channel amplifier. In the single channel mode, the OPTI-AMP transmitter allows the user to select which ear to record from. In the dual channel mode, the OPTI-AMP transmitter permits simultaneous transmission of data from both the contra and ipsilateral ears. The OPTI-AMP receiver provides eight adjustable amplification gain settings in addition to eight high-pass and low-pass filter settings. The electrode and transmitter system can also be configured as described in U.S. Pat. No. 5,099,856 to Killion et al., issued Mar. 31, 1992. The disclosure in Killion et al. is incorporated herein by reference thereto. Certain other features of the electrodes and associated circuitry can be found in U.S. Pat. No. 4,592,087, issued May 27, 1986 and U.S. Pat. No. 4,689,918, issued Aug. 25, 1987, which disclosures are incorporated herein by reference thereto.

Transmitter 20 may also be a high performance AC pre-amplifier manufactured by Grass Instrument Company of Quincy, MA. Particularly, a Grass Model P511 can be utilized to acquire evoked potential EEG signals. The Grass pre-amplifier can replace transmitter 20 and receiver 30. In that configuration, the output of the Grass amplifier is fed into an analog to digital converter on an input board. See item 910 in FIG. 17A.

In a preferred embodiment, the output of transmitter 20 is carried by optical cables 28 to a receiver 30. In one embodiment, receiver 30 is a board in a personal computer. In another embodiment, receiver 30 can be configured as a stand alone, peripheral device. For example, the OPTI-AMP device sometimes includes two discrete units, a transmitter unit and a discrete receiver unit. The receiver unit of the OPTI-AMP device can be coupled to an appropriate communications port in a computer.

In a preferred embodiment, the computer (the components to the right of transmitter 20 in FIG. 1) includes a 386 microprocessor as a central processing unit (CPU) 32 operating at speeds of 15-33 mhz. The computer includes memory 34 which, in one embodiment, is a 1 megabyte random access memory (RAM) and a 80 megabyte hard drive or storage memory unit. The computer also includes a co-processor or digital signal processing board (DSP BD) 34. In a current embodiment of the invention, the co-processing or DSP board is a processor board sold as Model No. TMS320C25 by Spectrum Signal Processing Inc. of Marborough, MA. The DSP board is a 16 bit, 100 ns processor running at speeds of 40–50 MHz. The board has a 544 word (16 bit) internal processor RAM and the board itself carries a 16k×16 45 ns RAM. The DSP board is connected not only to main computer bus 36, as is memory 34 and CPU 32, but also is directly connected to input/output board 40 via a 16 bit parallel expansion bus or cable 38.

Receiver 30 and input/output board 40 are described in detail later. However, in general, receiver 30 amplifies and filters the EEG analog signal received from transmitter 20 and supplies that signal via an analog bus or cable 42 to input/output board 40. Input/output board 40 has several functions, one of which is the conversion from analog to digital of the analog, filtered and buffered EEG signal stream from receiver 30. Another function of input/output board 40 is the generation of audio stimuli for headphones 12, 14. The particular details of receiver 30 and I/O board 40 for the current embodiment are discussed hereinafter with respect to FIGS. 17A and 17B.

The computer also includes standard input/output unit 44 which connects the computer to various peripheral devices such as a printer or plotter 46, a display or monitor 48 and a keyboard 50.

Figure 2A:
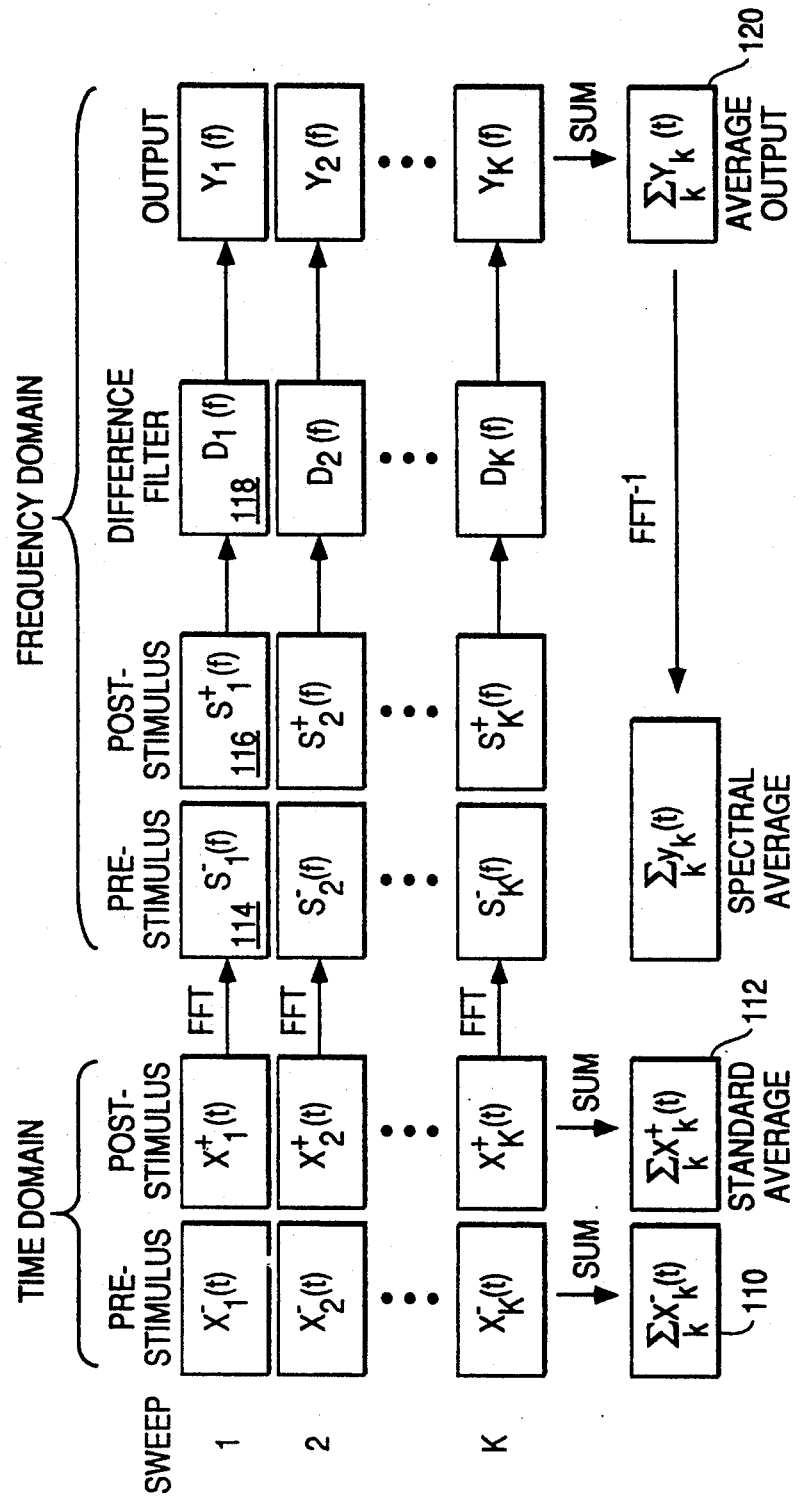
FIG. 2A diagrammatically illustrates spectral enhancement averaging and traditional averaging of pre- and post-stimulus EEG signals.

In one embodiment, the evoked potential processing system includes a spectral enhancement averaging routine. FIG. 2A diagrammatically illustrates both the traditional or standard averaging as well as the spectral averaging which is part of the present invention. In order to distinguish pre-stimulus EEG signal stream from a post-stimulus EEG signal stream, a − is used in conjunction with the pre-stimulus character and + is used in conjunction with the post-stimulus character. As used herein, the term "sweep" refers to a single pre-stimulus EEG signal stream linked to a single post-stimulus signal stream by a single stimulus. Since the evoked potential component in a particular EEG signal is quite small, on the order of 0.1 to 10.0 microvolts, and since there is a relatively large amount of noise or artifacts in the EEG signal, it is necessary to stimulate the patient a number of times and process the resulting consecutive EEG signal sets for further processing. An interlinked or sequential pre-stimulus EEG and post-stimulus EEG signal stream is referred to herein as a "single sweep" or as a single "EEG signal stream". Each sweep or set of signal streams has a time reference therein which, in the preferred embodiment, is keyed to the time of stimulation. The value of a signal segment in the time based EEG signal stream is then the value of the signal at a particular time or time segment relative to the time reference or stimulation time in each sweep or signal set.

In prior art devices, sweeps 1 through K of a time based pre-stimulus EEG signal from a plurality of would be summed together as shown in functional block 110. Also in prior art devices, sweeps 1 through K of a post-stimulus EEG signal streams would be summed together in as shown in function block 112. Averages can be obtained from these summed signal streams by dividing the time segment signals by K, the number of sweeps. The difference between the summed pre- and the post-stimulus time based EEG signal streams represents the typical or traditional averaging method to remove noise and artifacts from the evoked potential signals.

Figure 3B:
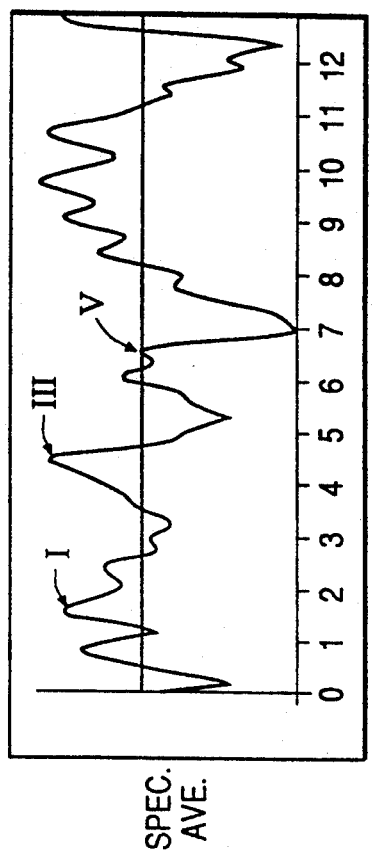
FIGS. 3A and 3B graphically illustrate a post-stimulus EEG signal streams processed with traditional averaging techniques and spectral enhancement averaging techniques, respectively.
Figure 3A:
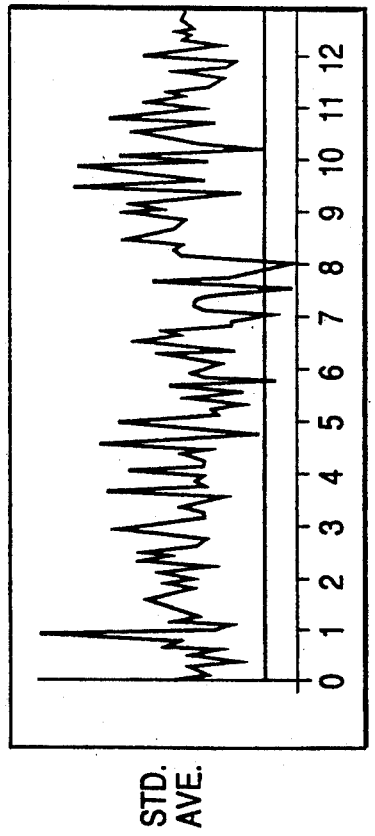

FIG. 3A graphically illustrates an EEG signal stream after the traditional averaging process. Particularly, FIG. 3A represents traditional averaging after 101 sweeps.

One embodiment of the present invention utilizes a spectral enhancement averaging technique. After obtaining the pre- and post-stimulation EEG signal streams for each sweep, those respective signal streams are converted into their frequency spectrum. A Fast Fourier Transform (FFT) conversion is utilized. After the conversion, a differential spectrum is obtained between the pre-stimulus frequency spectrum, functional block 114, and the post-stimulus frequency spectrum, functional block 116, to obtain a differential spectrum, functional block 118. The differential spectrum is obtained for all sweeps 1 through K. These differential spectrums are then summed by adding signal values, at coincidental time segments, together to obtain a summed differential spectrum as diagrammatically illustrated in functional block 120. The summed differential spectrum is then converted back into a time based signal stream utilizing the inverse of a Fast Fourier Transform. The resulting signal stream is graphically illustrated in FIG. 3B.

In FIG. 3B, the evoked potential (EP) signal is represented by a number of identifiable EP waveforms of which EP wave peaks I, III and V are marked. Accordingly, the evoked potential signal represented by spectral enhancement averaging of 101 sweeps is extremely clear as compared with standard or traditionally averaged signals shown in FIG. 3A.

To test the spectral enhancement averaging technique, spectral and standard averaging techniques were used to recover evoked potential signals from 512 single sweep auditory brain stem responses. Artificial noise consisting of random phase and frequency (0–2,000 Hz) tones at constant amplitude (10 times the average EEG amplitude) were added to the evoked potential signal stream. FIGS. 3A and 3B respectively show conventional or traditional averaging and the spectral enhancement averaging for 101 sweeps. A comparison between the traditional averaging technique and the spectral averaging technique for 512 sweeps also clearly shows that the spectral enhancement averaging method eliminates or significantly reduces artifacts and noise in the EEG signal such that the evoked potential waveforms can be easily identified and then stored for later analysis.

Spectral-enhanced averaging is based on the notion that the electrophysiological noise in EP (evoked potential) recordings is quasi-stationary such that its characteristics do not change appreciably within the short periods of time of a stimulus cycle, i.e., within the 24 ms acquisition window. If the pre- and post-stimulus response to the $k^{th}$ stimulus is denoted by $x^-{}_k(t)$ and $x^+{}_k(t)$ respectively, then $x^-{}_k(t) = n^-{}_k(t)$ and $x^-{}_k(t) = s^+{}_k(t) + n^+{}_k(t)$ where $s^+{}_k(t)$ is the deterministic post-stimulus signal and $n^-{}_k(t)$ and $n^+{}_k(t)$ are the random pre- and post stimulus noise.

Assuming the signal is deterministic and the same for every stimulus, $s^+{}_k(t) = s(t)$ The above equations can be written in the frequency domain as follows:

$$X_k^+(jw) = S(jw) + N_k^+(jw) \quad \text{Eq. 1}$$

$$X_k^-(jw) = N_k^-(jw) \quad \text{Eq. 2}$$

The pre- and post signals can be subtracted in the frequency domain to obtain the following:

$$Y_k^d = D\{X_k^+(jw) - X_k^-(jw)\} \quad \text{Eq. 3}$$

Since these signals are complex functions, the substraction can be done in a number of ways. The purpose of this operation is to reduce the noise signal N(jw). Equation 4 then applies.

$$E[Y_k^d(jw)] = 1/K \sum_{k=1}^{K} Y_k^d(jw) \quad \text{Eq. 4}$$

If the subtraction operation is properly chosen, the following equations can be written:

$$Y_k(jw) = S(jw) + E^d(jw) \quad \text{Eq. 5}$$

where $$E_k^d(jw) = 1/K \sum_{k=1}^{K} (N_k^+(jw) - N_k^-(jw))$$

assuming noise is quasi-stationary as described above, the Error term E is shown in equation 6.

$$E^d(jw) = \sum_{k=1}^{K} (N_k^+(jw) - N_k^-(jw)) \quad \text{Eq. 6}$$

The error term would decrease at a faster rate than $E^s(jw) = N^+_k(jw)$ which is the error term in standard ensemble or traditional averaging. Thus, frequency domain averaging of the post/pre response differences eliminates noise faster than standard averaging. The averaged response can be obtained easily after taking the inverse transform of the averaged $Y^d_k(jw)$ which approximates average X(jw).

The difference operation D can be performed in a number of ways. Taking the complex vector difference does not help since phase of noise at a given frequency can be drastically different in pre- and post-recordings. Taking only the magnitude of difference, however, solves this problem. Phase of the resulting signal remains the same as of the post-stimulus signal. When the magnitude of the pre-signal spectrogram value is greater than the post-signal spectrogram value, a zero value is assigned at that frequency. An alternative would involve taking the absolute value of the difference and adding 180° to the phase. Since the magnitude and frequency content of the artifact is likely to stay the same within the recording time of the single pre- and post-evoked potential, the artifact would be greatly reduced.

The use of frequency domain or spectral domain averaging is faster than standard or traditional ensemble averaging because fewer sweeps are necessary in order to obtain an identifiable evoked potential (EP) signal stream.

Figure 2B:
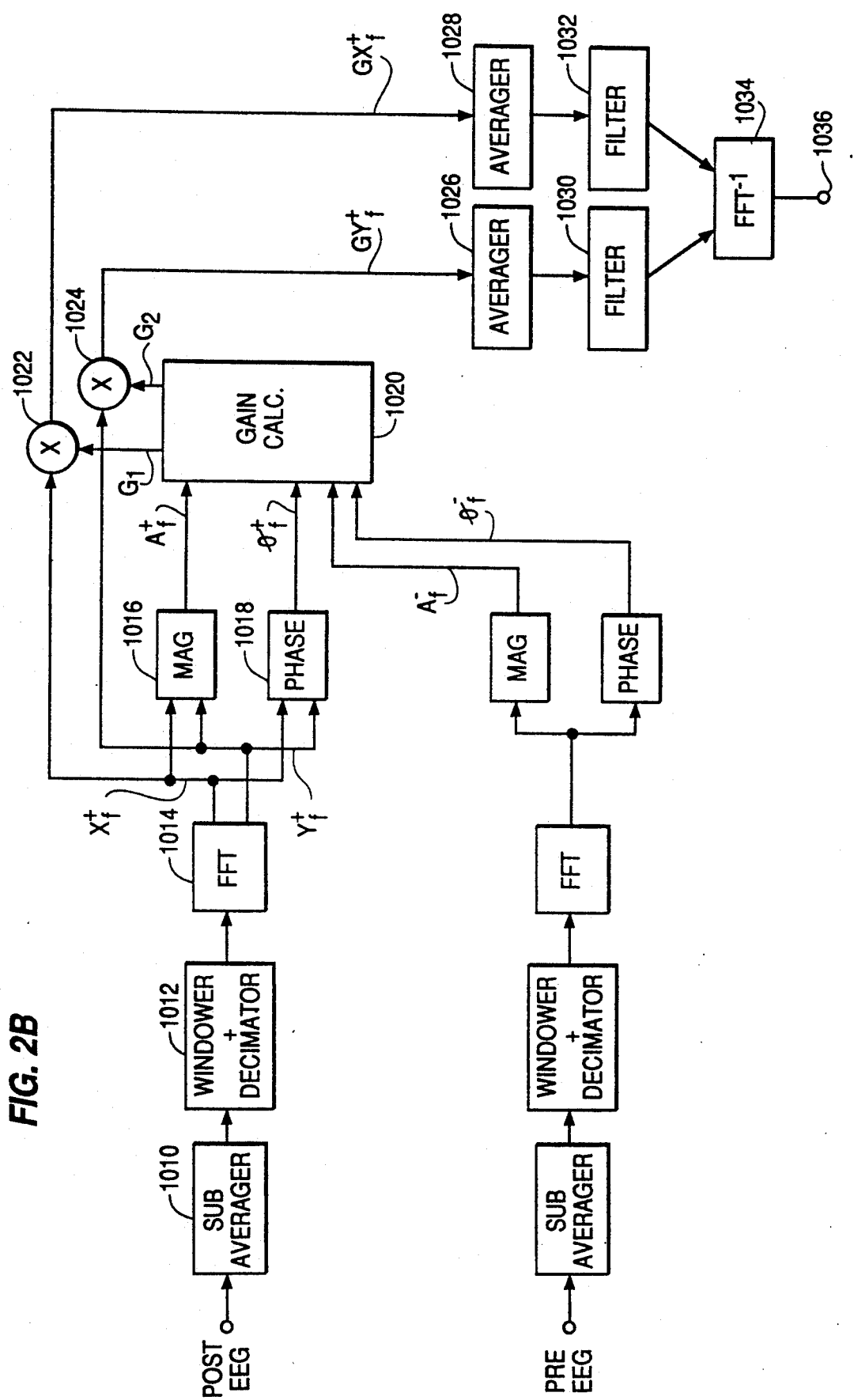
FIGS. 2B and 2C diagrammatically illustrate two systems to implement the spectral enhancement averaging technique illustrated in FIG. 2A.
Figure 2C:
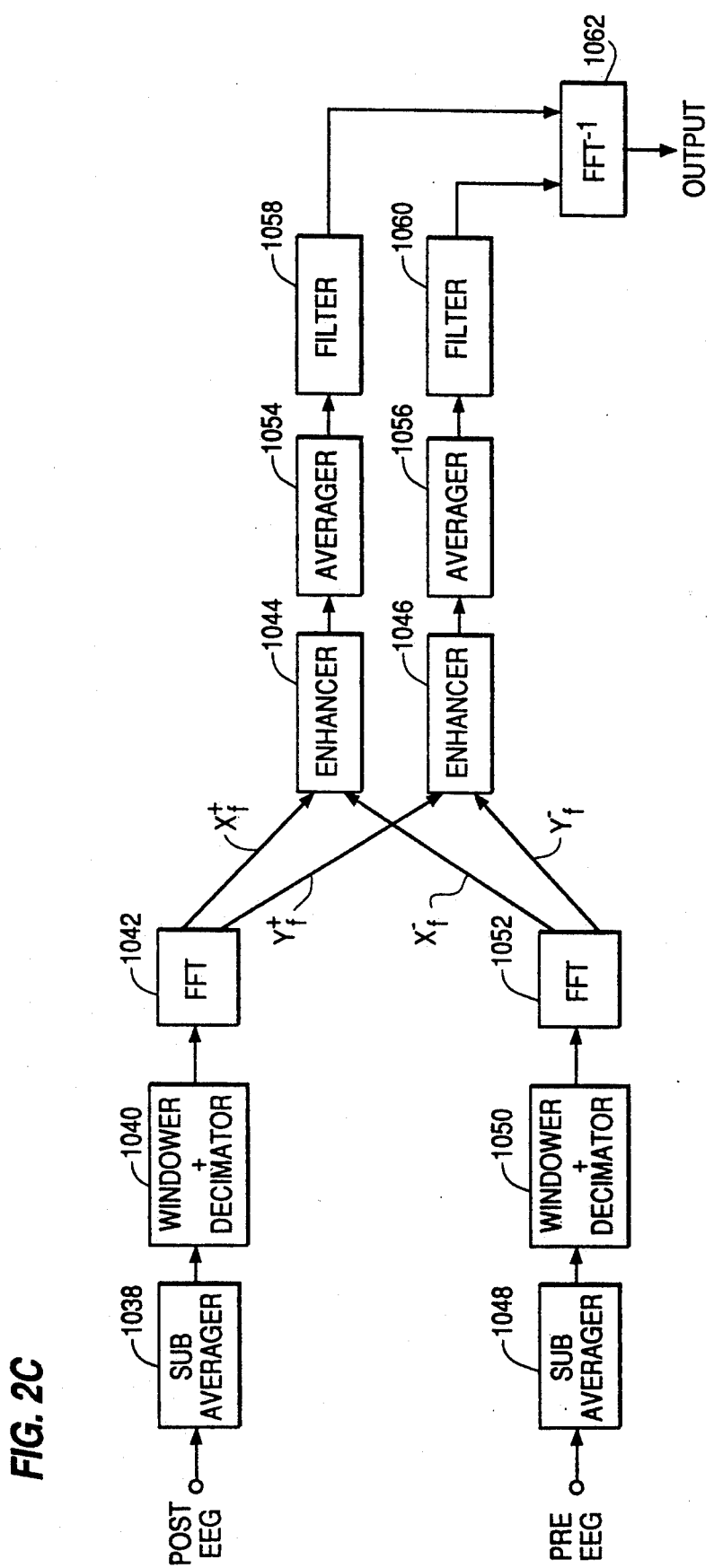

FIGS. 2B and 2C diagrammatically illustrate implementations to obtain the spectral difference signals. The functions in FIGS. 2B and 2C can be implemented by software or hardware.

FIG. 2B illustrates a phase dependent spectral enhancement implementation. In one embodiment, a predetermined number, e.g. 32, EEG signals, represented by 512 samples or signal segments (512 being an exemplary number), are summed in function step 1010. The summation step is optional. The summed signal is applied to windowing and decimation step 1012. The windowing step eliminates edge effects on the post-stimulus summed signal stream. The decimation (an optional step) removes pre-determined segments from the stream, e.g., in a 4:1 ratio, and reduces the stream to 128 samples. Step 1014 converts the signal stream into its frequency spectrum with an FFT function. The magnitude (MAG)$A_f^+$ and the phase $\phi_f^+$ of the real portion $X_f^+$ and the imaginary portion $Y_f^+$ of the resulting complex number representing the signal stream from FFT step 1014 is extracted by MAG step 1016 and phase step 1018. The magnitude $A_f^+$ and phase $\phi_f^+$ are applied to the calculate gain function 1020. The same operations are applied to the pre-stimulus EEG signal and the magnitude $A_f^-$ and phase $\phi_f^-$ are applied to the calculate gain function step 1020. The functions used in the gain calculator can be a standard magnitude difference where $G = A_f^+ - A_f^-$ or can be the absolute value of that difference signal or can be a negative truncated difference such that if $A_f^+ - A_f^-$ is less than or equal to zero, G is set as equal to the difference, but if the difference is greater than zero, G is set equal to the difference.

Function step 1020 generates a magnitude gain factor $G_1$, and a phase gain factor $G_2$. These gain factors are applied to the real and imaginary signals $X_f^+$ and $Y_f^+$ by multipliers 1022 and 1024. The multiplied signals $GX_f^+$ and $GY_f^+$ are summed over n sweeps by averaging steps 1026 and 1028. Filters 1030 and 1032 smooth the signals and the smoothed real and imaginary signals are applied to inverse FFT function step 1034. The output on line 1036 is the spectral averaged signal in a time base format.

FIG. 2C illustrates a phase dependent spectral enhancement implementation. The post-stimulus EEG signal is applied to averager 1038. Averager 1038 is optional. The averager may sum 32 sweeps or up to 256 sweeps. The summed signal is applied to window step 1040 which preferably includes a decimation step, (e.g. 4:1). The output is applied to FFT function 1042 and real and imaginary signal components $X_f^+$ and $Y_f^+$ are applied to enhance units 1044 and 1046, respectively. The pre-stimulus EEG signals are processed in the same manner with averager 1048, windower 1050, FFT 1052 and the real and imaginary signals are applied to units 1044, 1046. The enhancer units use the following formulas. If the frequency f is odd, $X_f^n$ is set equal to $X_f^+$ minus $X_f^-$ and $Y_f^n$ is set equal to $Y_f^+$ minus $Y_f^-$. If f is even, $X_f^n$ equals $X_f^+$ plus $X_f^-$ and $Y_f^n$ equals $Y_f^+$ plus $Y_f^-$. The real and imaginary signals are respectively applied to averagers 1054 and 1056. A predetermined number n sweeps are summed by units 1054 and 1056. The summed outputs are smoothed by filters 1058, 1060 (which are optional) and the smoothed signals are fed into inverse FFT unit 1062. The resultant is a time based signal which has been spectrally averaged.

In both the traditional averaging and the spectral enhanced averaging techniques, the system is set to acquire a predetermined number of pre- and post- EEG signal sets or sweeps. A variable sweep averaging or adaptive averaging technique can be utilized to limit the number of sweeps or data acquisition signal sets: During the averaging process, whether traditional or spectrally enhanced averaging, an estimate of the running signal to noise ratio SNR can be computed using the following computational formulas to monitor the improvement of the response signal, that is, the EP signal, with respect to the number of sweeps or sets averaged. An unbiased estimator formula has been proposed by Möcks et al., 1984, but the formula, Eq. C earlier, lacked a term, the reciprocal of K. Even with the term, Eq. C was not applied to both the pre- and post-stimulus signals. The modified formulas in accordance with the present invention follow:

where $SNR_R$ = Running signal to noise ratio estimate
$\hat{P}_s$ = Average signal power estimate
$\hat{P}_{\bar{n}}$ = Average noise power estimate
$x_k(t) = k^{th}$ EEG sweep or set
K = number of sweeps averaged
T = number of data points in each sweep.

$$\hat{SNR}_R^- = \frac{\hat{P}_s^-}{\hat{P}_n^-} \qquad \text{Eq. 7}$$

$$\hat{SNR}_R^+ = \frac{\hat{P}_s^+}{\hat{P}_{\bar{N}}^+} \qquad \text{Eq. 8}$$

$$\hat{P}_s = \frac{1}{T} \sum_{t=1}^{T} \bar{x}_k(t)^2 - \hat{P}_{\bar{n}} \qquad \text{Eq. 9}$$

$$\hat{P}_{\bar{n}} = \frac{1}{TK(K-1)} \sum_{t=1}^{T} \sum_{k=1}^{K} [x_k(t) - \bar{x}_k(t)]^2 \qquad \text{Eq. 10}$$

These equations, particularly Eq. 10, however, are practically impossible to compute in real time during a running average processing program. In addition to requiring many computations, all the single responses, that is, all the stored averages, must be kept in memory. The computations take longer and longer as the number of averaged sweeps K increases.

The present invention involves using a computational formula for $\hat{P}_{\bar{n}}$ which was obtained by algebraic manipulation of Eq. 10 above. The computational formula reduces the computation time to about 1/80th of the time required by the original formulas, Eq. 10 above. While the original formula, Eq. 10, requires the presence of all the single responses in memory, the computational formula Eq. 11 below requires the storage of the running sum of $x(t)$ and $x^2(t)$ only.

$$\hat{P}_{\bar{n}} = \frac{1}{TK(K-1)} \sum_{t=1}^{T} \left[ \sum_{k=1}^{K} x_k^2(t) - \frac{1}{K} \sum_{k=1}^{K} x_k(t) \sum_{k=1}^{K} x_k(t) \right] \qquad \text{Eq. 11}$$

Figure 5:
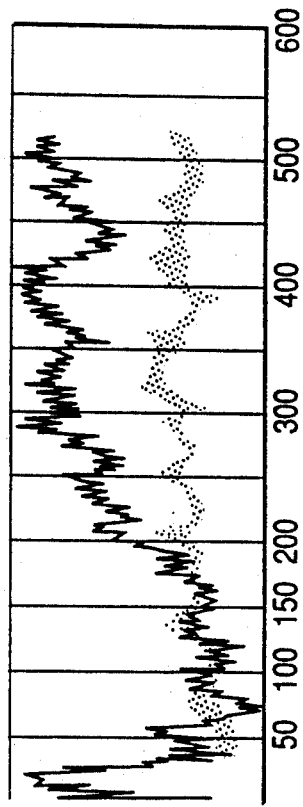
FIGS. 5, 6, 7, and 8 graphically illustrate the estimated running signal to noise ratio at 0 dB, 10 dB, 30 dB, and 40 dB using the computational formulas developed in accordance with the principles of the present invention.
Figure 6:
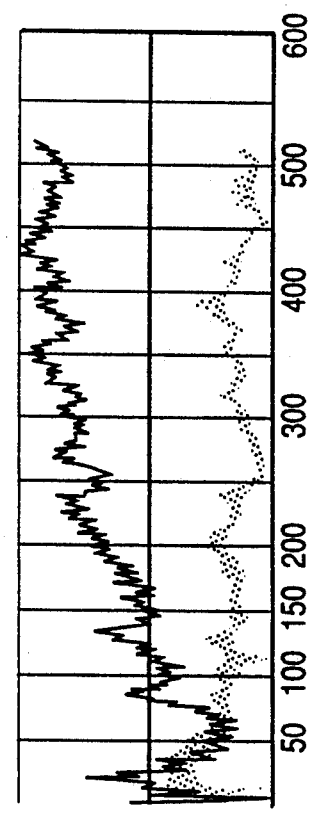

The running estimate $SNR_R$ value can be calculated each time when a new single sweep is averaged and used for response detection. FIGS. 5, 6, 7 and 8 show the summed average for n sweeps with 0 dB, 10 dB, 30 dB and 40 dB hearing level clicks stimulating a subject. FIG. 5 shows the running SNR values for the pre-stimulus values in dotted lines and the post-stimulus SNR in solid lines and further shows that at 0 dB, the function for the pre- and post-averages stays flat since there is no response in the average eventhough the number of sweeps exceeds 500. The subject's psychophysical threshold for this stimulus was 5 dB hearing level.

Figure 7:
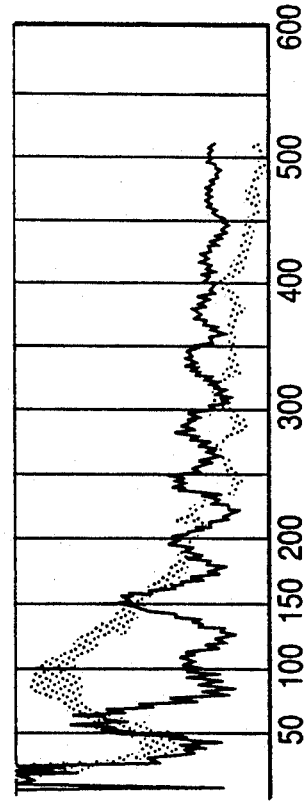
Figure 8:
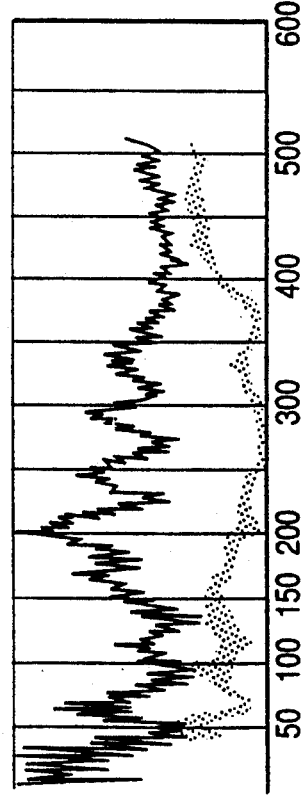

Graphs 6, 7 and 8 show, respectively, results at 10 dB, 30 dB and 40 dB hearing level clicks. These supra threshold $SNR_R$ values for pre-(dotted) and post-(solid) averages separate or diverge after about 100 to 150 sweeps. For example, in FIG. 6, the estimated running SNR values of the pre- and the post-values separate at about 135 sweeps. In FIG. 7, the pre- and post-SNR values separate at about 185 sweeps. In FIG. 8, the pre- and post-SNR values separate at about 75 sweeps. A simple difference detector can be used to detect this separation between the pre- and post-estimated running SNR values to determine the presence of an adequate response for automated threshold determination.

If the pre- and post-stimulus estimated running signal to noise ratio is denoted $SNR^-_R$ and $SNR^+_R$, respectively, then a stop averaging command can be generated when the absolute value of the difference is less than a predetermined threshold $AVE_{th}$.

Figure 4:
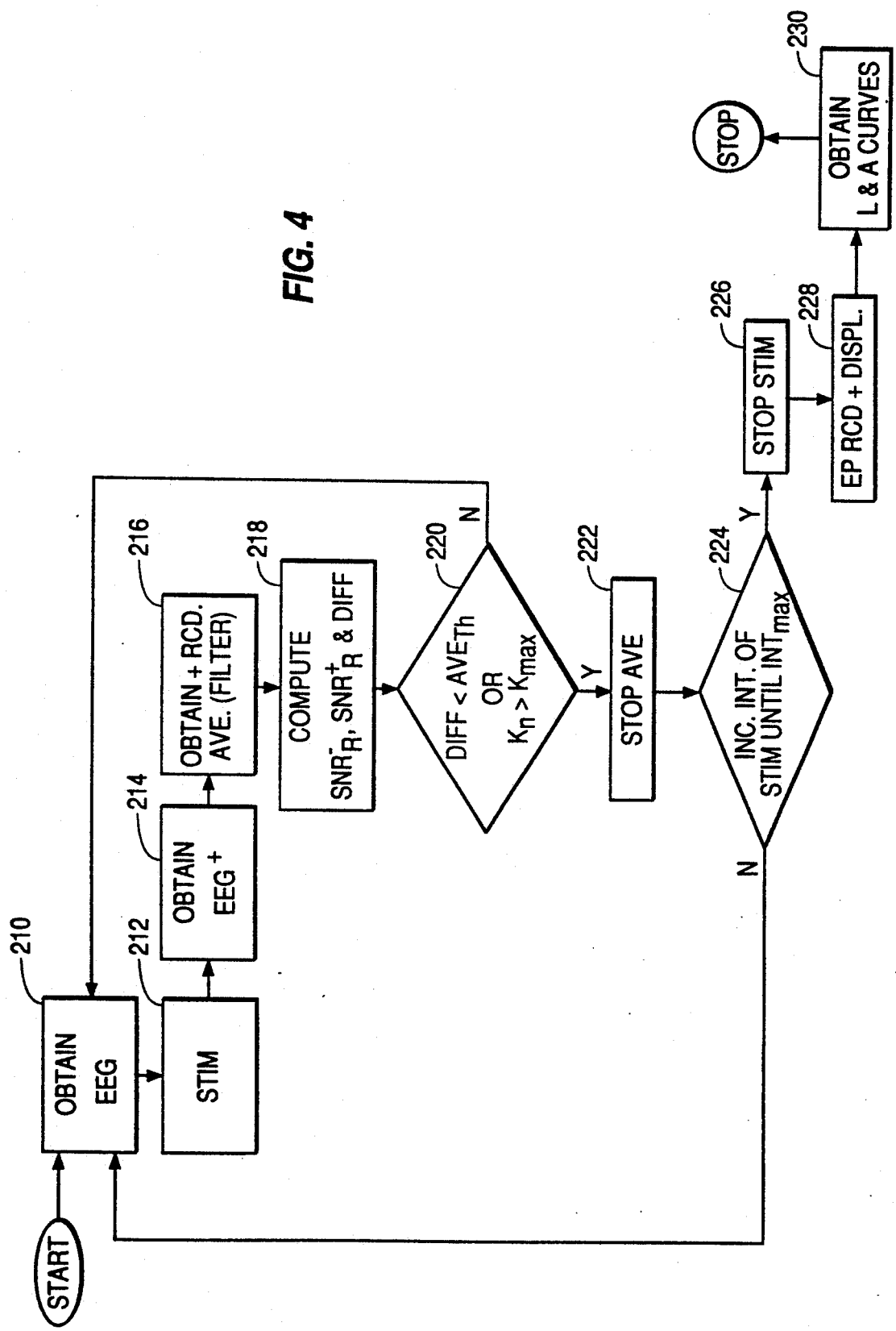
FIG. 4 diagrammatically illustrates a general flow chart used in conjunction with the adaptive averaging technique in accordance with the principles of the present invention.

FIG. 4 diagrammatically illustrates a simple flow chart to implement the variable averaging technique. Step 210 obtains the EEG signal stream. Step 212 stimulates the subject. Step 214 obtains the post-stimulus EEG signal. Step 216 obtains and records the pre- and post-averages. See, for example, the time domain route in FIG. 2. This averaging acts as a filter. Step 218 computes the estimated running signal to noise ratio as shown in Eqs. 7, 8, 9 and 11 above. These equations require the storage of the running sum of $x(t)$ and $x^2(t)$. Decision step 220 determines whether the difference between the pre-stimulus SNR and post-stimulus SNR values is less than a threshold average $AVE_{th}$. Alternatively, if the number of sweeps of pre- and post-EEG sets exceeds $K_{max}$, the YES branch is taken to a stop averaging routine 222. If the difference is greater than the averaging threshold, the NO branch is taken the system obtains the next sequential pre-stimulus EEG signal in step 210. Assuming the threshold has been met, or the gross number of sweeps has been obtained, $K_n$ being greater than $K_{max}$, the YES branch is taken and the system stops averaging and also stops stimulating the subject. Decision step 224 determines whether the intensity of the stimulus should be increased or whether the frequency of the stimulus should be changed. If a click stimulus is used, the intensity of the click may be increased. If a frequency tonal burst is being used, the tone or frequency value of that stimulus would be increased. If the maximum intensity has been reached, $INT_{max}$, the YES branch is taken and the stimulus is stopped as noted by function block 226. If the maximum intensity has not been reached, the NO branch is taken from decision step 224 and the system obtains the next pre-EEG signal in step 210. Once the stimulus has stopped, the system, in step 228, identifies the evoked potential (EP) signal and records and displays the signal. In step 230, the latency-intensity curves are obtained (L curves) and audiograms are also obtained (A curves).

Experiments have shown that if the Möcks' prior art equation, that is Eq. D, as modified with the inverse of K is used, it takes about two hours to compute the estimated signal to noise ratio. The SNR threshold ratio $AVE_{th}$ is set, in one embodiment, at 0.3. Using the discovered computational formula, Eq. 11, the present system, in real time, adaptively determines the number of sweeps needed to identify the evoked potential signal.

The present invention also relates to the use of a two-dimensional filtering system to eliminate artifacts and noise in the EEG signal streams.

One prior art system suggested the use of a two-dimensional filter but only used that filter in conjunction with stimuli having a constant intensity and frequency. That prior art reference, by Sgro et al. (1985), did not suggest the use of a two-dimensional filter and altering the intensity of the stimuli or changing the frequency (tonal quality) of the stimuli and comparing the resultant evoked potential waveform signals.

Figure 9:
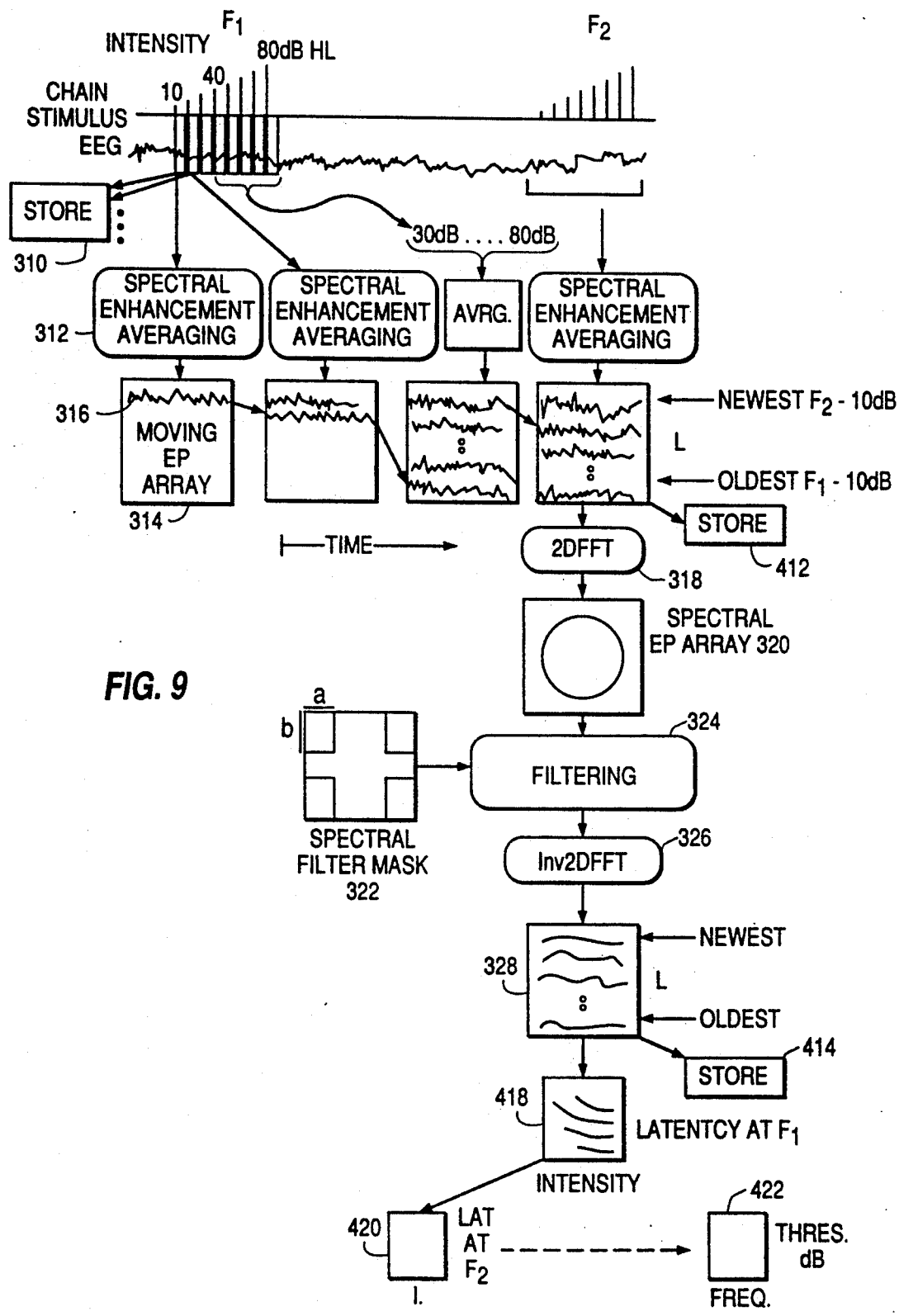
FIG. 9 diagrammatically illustrates data flow and processing techniques for the two-dimensional filter in accordance with the principles of the present invention.

FIG. 9 shows an expanded data flow diagram showing several features of the present invention combined into a single system. A chain of stimuli is directed at the subject. The intensity of the stimuli is varied in 10 dB hearing level steps from 10 dB through 80 dB. The frequency of the first super group is set at frequency $F_1$. In each group of stimuli having the same intensity, for example a 10 dB intensity, there is a plurality of stimuli. For example, 512 stimuli in each group. The EEG signals from the subject are monitored and pre- and post-stimulus EEG signals are stored as noted in function step 310. A sub-group of the EP signals at 10 dB stimuli, for example, 32 sweeps (or up to 256 sweeps), are processed through the spectral enhancement averaging as diagrammatically illustrated above with respect to FIG. 2. This spectral averaging is identified in functional block 312 in FIG. 9. A sub-group of these 10 dB intensity group would be spectrally averaged together and the resulting time domain signal would be obtained and loaded into moving EP array 314. The time based, spectral averaged signal is diagrammatically illustrated as waveform 316 in FIG. 9. Subsequent spectrally averaged sub-groups would be loaded into the EP array on a first in, first out basis. When the array is full with K sub-groups of spectral enhanced averaged sweeps, the array is filtered with a two-dimensional filter.

In one embodiment, a two-dimensional Fast Fourier Transform (FFT) filter is utilized. This is illustrated as function step 318 in FIG. 9. The spectral EP array 320 is then subjected to a masking step 324 by spectral filter mask 322. Mask 322 is a rectangular mask. The mask zero pads the array in both x and y (a and b) directions to prevent leakage and circular convolution effects. The filtering/masking step is shown as function block 324. For example, array 320 is a 64×64 point array. Value a is set at 1640.63 Hz and acts as a low pass filter on a particular sweep. Value a is the cut-off frequency for the filter. Value b is set at 390.63 spatial Hz and acts as a low pass filter on the aligned signal segments in adjacent sweeps. Alternatively, a two-dimensional Gaussian filter can be used as shown in Eq. 12.

$$f(x, y) = \exp\left(-\frac{1}{2}\left(\sqrt{\frac{x_1}{CG_1}} + \sqrt{\frac{y_1}{CG_2}}\right)\right) \quad \text{Eq. 12}$$

C = 1.925
$x_1 = x (\cos (2\pi G_3/360)) - y (\sin (2\pi G_3/360))$
$y_1 = x (\sin (2\pi G_3/360)) - y (\cos (2\pi G_3/360))$
$G_1$ = major axis parameter 3 dB down point;
$G_2$ = minor axis parameter 3 dB down point;
$G_3$ = angle with respect to x axis The masked spectral EP array is then re-converted from the frequency domain by a two-dimensional inverse FFT conversion, shown in step 326, into the time domain. A resulting two-dimensional time based array, diagrammatically illustrated as function 328, shows at its lower end the oldest recording and at its top end the most recent fully filtered recording.

Figure 10:
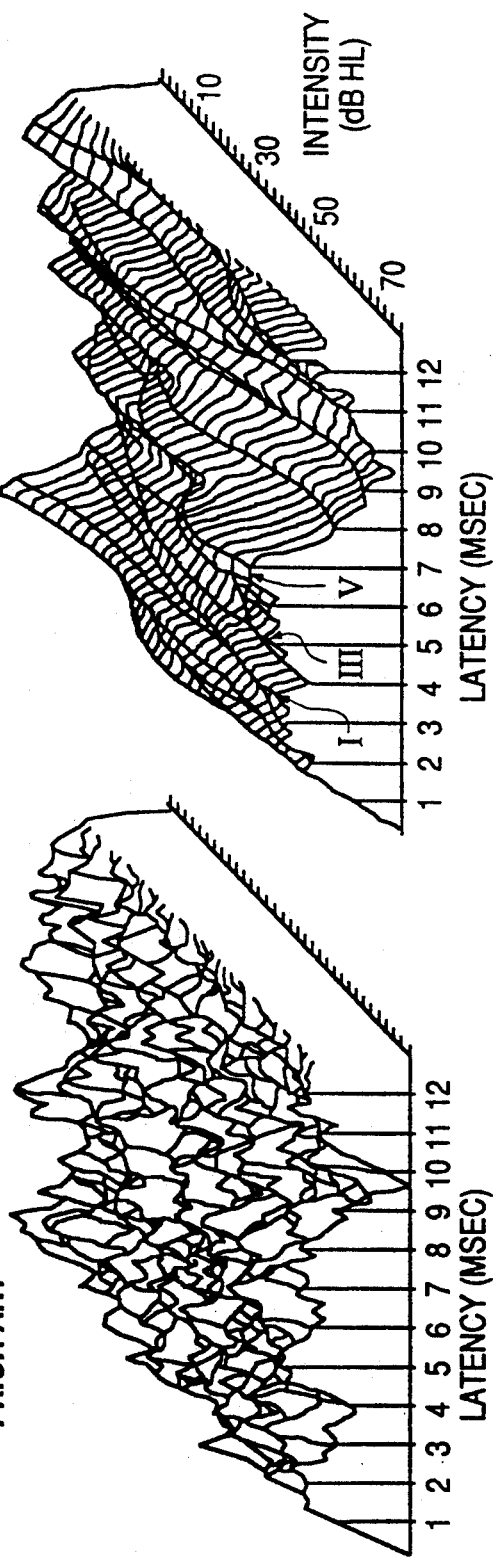
FIG. 10 graphically illustrates a three-dimensional plot of consecutive, conventionally filtered (standard averaging) evoked potential signals.

FIG. 10 shows a three-dimensional plot of conventionally averaged, sequential auditory brain stem responses (ABRs) acquired with averaging 32 sweeps. This represents a two-dimensional array of signals with the time base of each summed signal aligned with all other summed signal sets. Each line represents the sum of, for example, 32 sweeps. The intensity is increased 5 dB after every fourth sum. The latency time in milliseconds is shown on the abscissa or x axis. On the z axis, recording sequence is shown.

Figure 11:
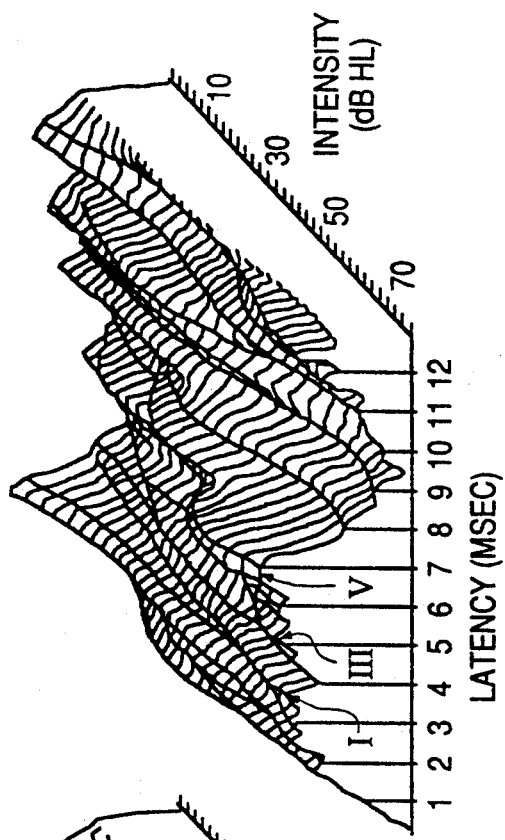
FIG. 11 graphically illustrates the EP data processed with a two-dimensional filter in accordance with the principles of the present invention.

FIG. 11 shows the same EEG recordings after processing with a two-dimensional filter. It can easily be seen that the evoked potential waveforms I, III, and V are visibly present and ascertainable as compared to FIG. 10. The prior art devices did not change the frequency or the intensity of the stimuli.

Although FIG. 9 shows the use of spectral enhancement averaging as well as the two-dimensional filter and the varying intensities and frequencies, the present invention can be configured with just the spectral enhancement averaging. The present invention can also be configured with just the two-dimensional filtering at different frequency levels or different intensity levels for the stimuli. The ordering of the stimuli may be changes such that the frequency is increased at a certain intensity level. The variable adaptive averaging limit could be incorporated into an EP processing system without significant difficulty.

In order to compile and keep adequate records, the oldest spectral average is stored in function block 412 before that signal is discarded from moving EP array 314. Also, the two-dimensionally filtered EP signal is stored as shown by function block 414. These filtered EP signals can be further processed to form latency-intensity curves at various frequencies, for example, at frequency $F_1$ latency curve 418 could be constructed. At frequency $F_2$, latency curve 420 can be constructed. Later, an audiogram 422 can be constructed by the system by application of a predetermined number of frequencies $F_i$.

FIG. 12 diagrammatically illustrates a latency-intensity curve. Blocked regions 512, 514 and 516 define "normal" regions for latency EP peak V (region 512), EP peak III (region 514), and EP peak I (region 516). Latency shows the time delay between the stimulus and the presence of a certain evoked potential waveform at certain frequencies. FIG. 13 diagrammatically illustrates a display screen of the monitor showing the current intensity level 50 dB hearing level (HL), the latency in milliseconds, and the inter-peak intervals. Also, the stimulation is shown as a click and not as a particular frequency or tonal burst.

FIG. 13 diagrammatically illustrates an audiogram showing, on the abscissa, the frequency in kilohertz and, on the ordinate, the threshold intensity level in dB hearing level.

Figure 16:
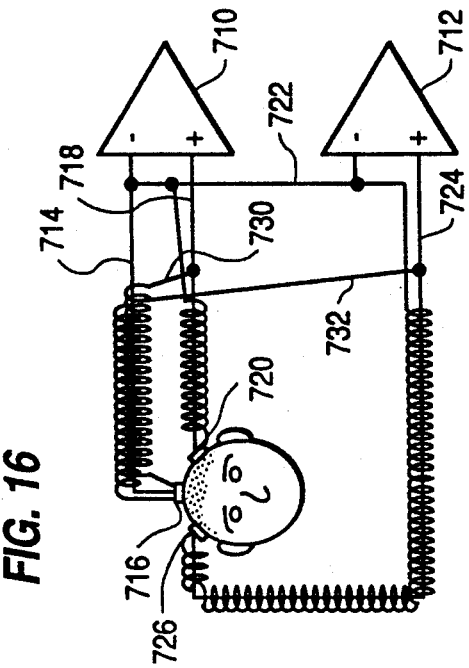
FIG. 16 diagrammatically illustrates another electrode wire configuration for a three electrode system in accordance with the principles of the present invention.
Figure 15:
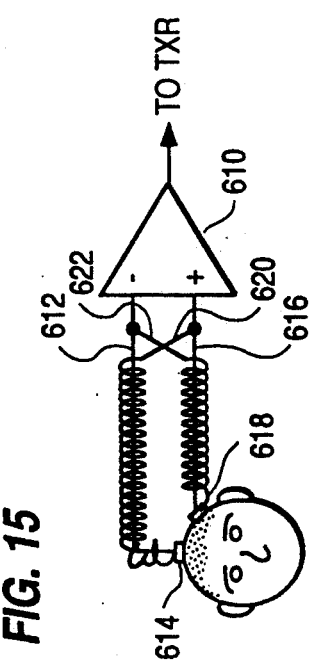
FIG. 15 diagrammatically illustrates one electrode wire configuration in accordance with the principles of the present invention.

FIGS. 15 and 16 diagrammatically illustrate new electrode wiring systems which may be used in conjunction with the evoked potential system. FIG. 15 diagrammatically illustrates a single ended, ground free amplifier electrode wiring configuration. Bioamplifier 610 has a positive input and a negative input. Electrode wire 612 is electrically connected to electrode 614 and the negative input of bioamplifier 610. Electrode wire 616 electrically connects electrode 618 and the positive input of bioamplifier 610. Shielding for electrode wire 612 is electrically connected to electrode wire 616 by jumper 620. The shielding for electrode wire 616 is electrically connected to electrode wire 612 by jumper 622. Bioamplifier 610 is ground free and the cross-wired shields eliminate noise affecting the respective shielded electrode wires 612 and 616. Wires 612 and 616 are coaxial, shielded wires and the cross wires are connected to the shields.

FIG. 16 shows a single ended, ground free electrode configuration for three electrodes. Bioamplifiers 710 and 712 each have two inputs, a positive input and a negative input. Electrode wire 714 is electrically connected to electrode 716 and the negative terminal of bioamplifier 710. Wire 716 has two coaxial shields thereon. Electrode wire 718 electrically connects electrode 720 and the positive input of bioamplifier 710. The negative electrode of bioamplifier 712 is electrically connected to electrode wire 714 by jumper 722. Electrode wire 724 electrically connects electrode 726 to the positive input of bioamplifier 712. One coaxial shield for electrode 714 is electrically cross connected to electrode wire 718 by jumper 730. The other coaxial shield is electrically cross connected to electrode wire 724 by jumper 732. Electrode 714 is double shielded by being separately cross connected to electrode wires 718 and 724, respectively by jumpers 730 and 732. The shields for electrode wires 718 and 724 are cross connected to electrode wire 714 by jumper 722. This shielding configuration eliminates artifacts in the EEG signals that are carried by electrode wires 714, 718 and 724.

Figure 17A:
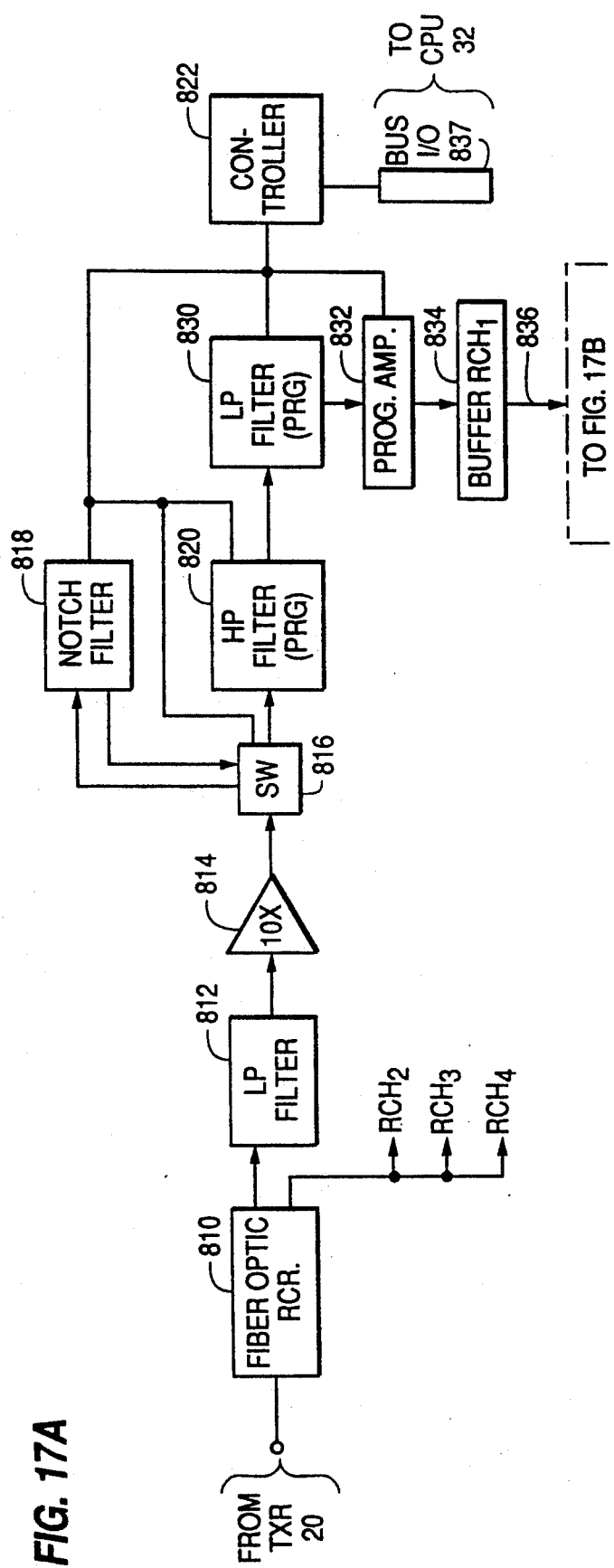
FIGS. 17A and 17B diagrammatically illustrate hardware block diagrams showing a receiver and a input/output board, respectively.

FIG. 17A diagrammatically illustrates the receiver board in the evoked potential system generally identified as receiver board 30 in FIG. 1. In FIG. 1, optical cables 28 are coupled to receiver 30. One channel of those optical cables is attached to a fiber optic receiver 810 in FIG. 17A. The fiber optic receiver is manufactured by Hewlett-Packard and is called a Modulus Model HP2521. The output of optic receiver 810 is a pulse width modulated signal. The output of optic receiver 810 is fed to a low-pass filter 812. The low-pass filter acts as an integrator and is set at 10 kHz. The output of low-pass filter 812 is fed to an amplifier 814 which, in the working embodiment, amplifies the signal ten times. The output of the amplifier is fed to a switch 816 which can channel the signal into and out of a notch filter 818. Switch 816 either channels the signal into notch filter 18 or channels the signal directly to a high-pass programmable filter 820. In the working embodiment, the notch filter is set at 60 Hz thereby passing all signals except 60 Hz signals therethrough. Switch 816 is controlled via software commands and, hence, is coupled to a controller 822. Controller 822 is connected to the main bus in the computer via input/output port 857.

The high-pass filter is also software programmable and is controlled by signals sent by controller 822. In an working embodiment, the high-pass programmable filter 820 can be set at eight different frequencies to eliminate certain low frequencies. Table 1 which follows shows these frequencies.

TABLE 1

| |
| --- |
| 0.3 Hz |
| 1.0 Hz |
| 3.0 Hz |
| 10 Hz |
| 30 Hz |
| 100 Hz |
| 300 Hz |
| 500 Hz |

The output of the high-pass filter 820 is fed to a programmable low-pass filter 830.

The low-pass filter filters out certain high frequencies as commanded by controller 822.

Table 2 which follows shows that the low-pass filter can be programmably set to one of eight different frequencies.

TABLE 2

| |
| --- |
| 30 Hz |
| 100 Hz |
| 300 Hz |
| 500 Hz |
| 1000 Hz |
| 3000 Hz |
| 5000 Hz |
| 10000 Hz |

The output from low-pass filter 830 is applied to a programmable amplifier 832. Amplifier 832 is controlled by controller 822 and can be set to varying levels as shown in Table 3.

TABLE 3

| |
| --- |
| 5 X |
| 10 X |
| 20 X |
| 50 X |
| 100 X |
| 150 X |
| 200 X |
| 300 X |

The output of programmable amplifier 832 is applied to buffer 834 which handles the received channel 1, $RCH_1$. The buffer provides an isolation for the analog signal and isolates the output of the buffer from the rest of the receiver circuitry. The output of buffer 834 is applied to a shielded external cable 836 extending between the receiver board in the computer to the input/output 40 in the computer. In the working embodiment, shielded cable 836 is a four channel twisted pair. The receiver board is adapted to handle four channels $RCH_2$, $RCH_3$, $RCH_4$. The circuitry for receiver channels 2, 3 and 4 is substantially the same as channel 1 discussed in detail herein. Up to five electrodes can be used with single ended ground free bioamplifiers. If differential bioamplifiers are used, up to eleven electrodes can be used. Two electrodes are needed for each channel of information.

Figure 17B:
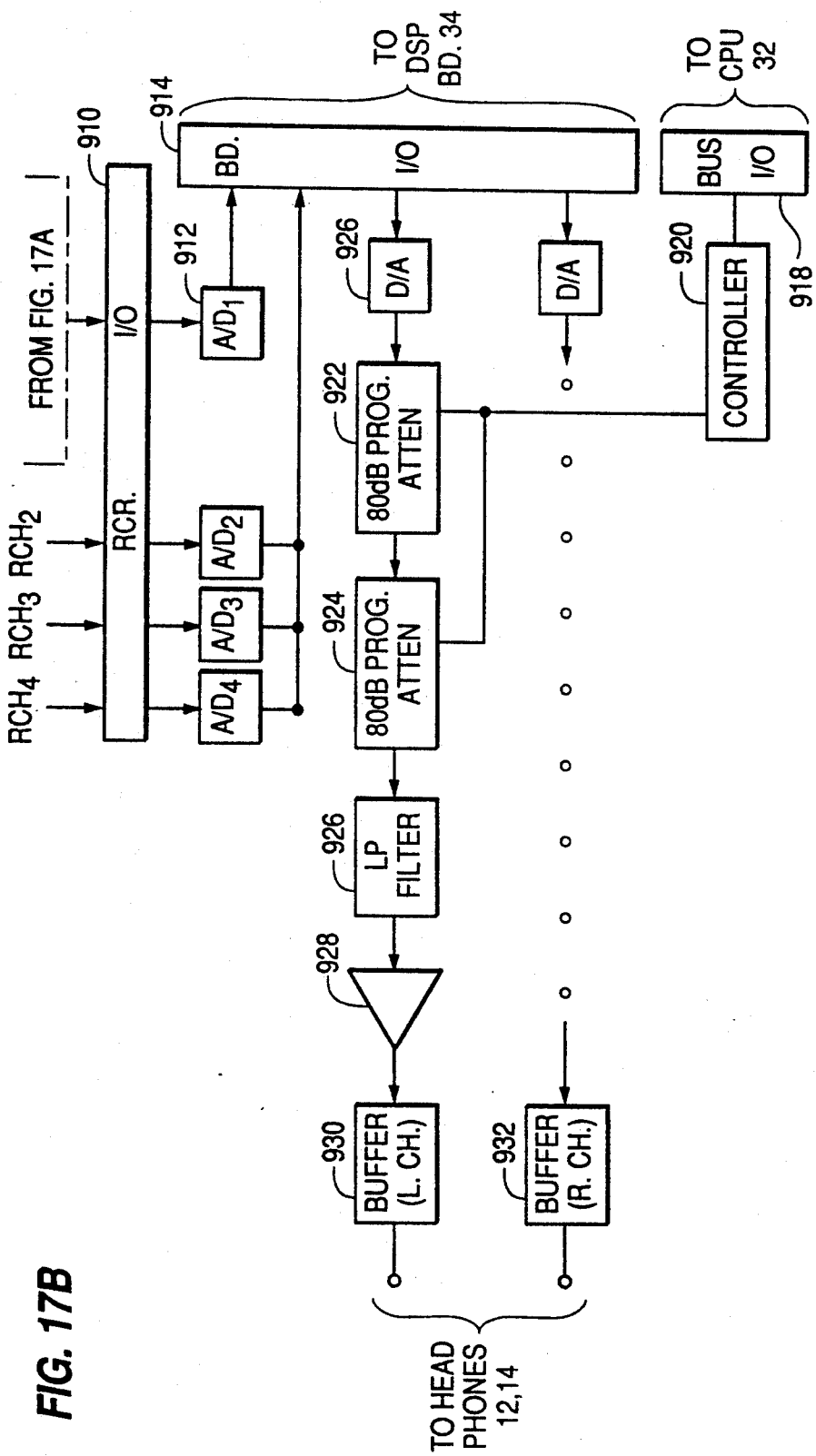

FIG. 17B diagrammatically illustrates the major components in the input/output board 40 of FIG. 1. One function of the input/output board 40 is converting the analog signal from the buffers for the various received channels into digitally formatted signals. Accordingly, the input/output board includes a receiver input/output port 910. Each channel has an associated analog to digital converter such as $A/D_1$ 912 for channel 1. The output of $A/D_1$ 912 is applied to an input/output port 914 linked to the DSP board 34. The input/output port is identified as port 914 in FIG. 17B. The outputs from the analog to digital converters are separately applied to the input/output port 914 and fed to the DSP board 34 upon receipt of the proper control signal.

Another function of the input/output board is to generate stimuli for the subject. Control signal from CPU 32 are received by the bus input/output port 918 and are handled by controller 920. The controller provides commands for a pair of programmable attenuators 922 and 924. The data processing board 34 applies signals through the board input/output port 914 to a digital to analog converter 926. The analog signal from D to A converter 926 is fed to an 80 dB programmable attenuator 922. Programmable attenuator 922 and programmable attenuator 924 each attenuate the signal from 0 through 80 dB. The output of the second programmable attenuator 924 is fed to a low-pass filter 926. In a working embodiment, low-pass filter 926 is set at 10 kHz. The output of low-pass filter 926 is fed to an amplifier 928 and ultimately to a buffer 930. Left channel buffer 930 and the right channel buffer 932 condition the signals which are ultimately applied to headphones 12 and 14 shown in FIG. 1. A detailed description of the left channel is shown for the input/output board in FIG. 17B. The right channel is processed in the same manner as discussed above with respect to the left channel.

The claims appended hereto are meant to cover modifications and changes within the spirit and scope of the present invention.

What is claimed is:

1. Method of obtaining an evoked potential signal from a digitally formatted, pre- and post-stimulation electroencephalographic (EEG) signal stream comprising the steps of:
    obtaining a digitally formatted pre-stimulus EEG signal stream;
    converting said pre-stimulus EEG signal into a pre-stimulus frequency spectrum signal;
    stimulating EEG activity with a plurality of predetermined stimuli;
    obtaining a digitally formatted post-stimulus EEG signal stream;
    converting said post-stimulus EEG signal into a post-stimulus frequency spectrum signal;
    obtaining a differential spectrum from said pre- and post-stimulus frequency spectrum signals;
    converting said differential spectrum into a time based signal stream which contains said evoked potential signal therein; and,
    identifying said evoked potential signal in said time based signal stream and storing the same.

2. A method as claimed in claim 1 including processing an evoked potential signal from a plurality of digitally formatted, pre- and post-stimulation electroencephalographic (EEG) signal streams and including the steps of:
    locating, in each interrelated set of pre- and post-stimulation EEG signal streams, a time reference present in all such sets in said plurality of EEG signal streams;
    after conversion into the frequency spectrum, obtaining a respective differential spectrum from each said set of pre- and post-stimulus frequency spectrum signals;
    summing said differential spectrums by correlating respective time bases in each differential spectrum with the respective time reference in each set and summing time coincidental segments in each differential spectrum together; and
    converting the summed differential spectrum into a time based signal stream which contains said evoked potential signal therein.

3. A method as claimed in claim 2 including the step of stimulating EEG activity with a plurality of timed stimuli, said time reference in each set being correlated to said stimuli.

4. A method as claimed in claim 3 wherein the step of stimulating uses one of auditory stimulation, visual stimulation or somato sensory stimulation.

5. A method as claimed in claim 4 wherein said auditory stimulation is one of a click or a frequency specific auditory stimulus.

6. A method as claimed in claim 3 including the steps of:
    separately averaging said pre-stimulus and a post-stimulus EEG signal streams over an increasing K number of sets of pre- and post streams;
    calculating a time based average noise power $P^-_n$ and $P^+_n$ for said pre-stimulus and post-stimulus EEG signal streams respectively over K number of sets with the formula:

$$\hat{P}_n = \frac{1}{TK(K-1)} \sum_{t=1}^{T} \left[ \sum_{k=1}^{K} x_k^2(t) - \frac{1}{K} \sum_{k=1}^{K} x_k(t) \sum_{k=1}^{K} x_k(t) \right]$$

where
   $x_k(t) = k^{th}$ EEG set,
   T = number of data points in each sweep, and
   $\hat{P}^-_{\bar{n}}$ = time based pre-stimulus average noise power;
   $\hat{P}^+_{\bar{n}}$ = time based post-stimulus average noise power
   calculating a time based average signal power $P^-_s$ and $P^+_s$ for said pre-stimulus and a post-stimulus EEG signal streams respectively over K number of sets with the formula:

$$\hat{P}_s = \frac{1}{T} \sum_{t=1}^{T} \bar{x}_k(t)^2 - \hat{P}_{\bar{n}}$$

calculating a pre- and post-stimulus, estimated, running signal to noise ratio SNR−, SNR+ from the respective ratio of the pre- and post-stimulus average signal powers Ps−, Ps+ and average noise powers Pn−, Pn+;
   stopping said averaging step when the difference between said pre- and post-stimulus running signal to noise ratios is less than a predetermined threshold and at K number of sets; and
   limiting the number of differential spectrums to be summed to K number.

7. A method as claimed in claim 6 wherein the steps of calculating Pn−, Pn+ Ps−, Ps+ and SNR−, SNR+ occurs continually in real time with respect to the steps of obtaining the pre- and post-stimulus EEG signal streams.

8. A method as claimed in claim 3 wherein the step of stimulating includes stimulating with a plurality of timed and grouped stimuli, each stimulus in a group of stimuli having one of substantially the same intensity level or substantially the same frequency, and respective groups of stimuli having increasing levels of intensity or frequency stimuli;
    wherein the step of summing said differential spectrums by correlating respective time bases, sums all differential spectrums in a respective sub-group;
    thereafter, the summed differential spectrum for each sub-group is converted into a time based sub-group signal stream representing each sub-group, and the same resulting in a first filtered EEG signal stream;
    forming an array of EEG signal streams with at least a portion of first filtered EEG signal streams resulting from said group of stimuli, wherein the respective time bases of the first filtered streams are correlated together and are keyed to a respective time reference in each first filtered EEG signal stream; and filtering said array with a two-dimensional filter; and identifying a plurality of evoked potential signals in the filtered array and storing the same.

9. A method as claimed in claim 8 wherein the array includes first filtered EEG signal streams resulting from at least two groups of stimuli, thereby representing at least two levels of intensity or frequency stimulation.

10. A method as claimed in claim 8 wherein the time bases in the first filtered EEG signal streams in said array are aligned.

11. A method as claimed in claim 8 wherein said two-dimensional filter operates in the frequency domain.

12. A method as claimed in claim 8 wherein the step of filtering said array includes the steps of:

transforming said array into a frequency domain using a two-dimensional Fast Fourier Transform;

masking predetermined two-dimensional regions of the transformed array; and inversely transforming said masked array with a two-dimensional inverse Fast Fourier Transform.

13. A method as claimed in claim 12 wherein the masking step zero pads predetermined regions in the transformed array in each dimension.

14. A method as claimed in claim 12 wherein the masking step prevents leakage and circular convolution effects in the transformed array.

15. A method as claimed in claim 3 wherein an increasing number K of stimuli are used in the stimulation step and includes the steps of:

calculating a pre- and post-stimulus, estimated, running signal to noise ratios from respective pre- and post-stimulus average signal powers and average noise powers of the pre- and post-EEG signal streams;

stopping the summation of said differential spectrums and the stimuli and establishing K when the difference between said pre- and post-stimulus running signal to noise ratios is less than a predetermined threshold.

16. A method as claimed in claim 1 wherein the step of identifying said evoked potential signal in said time based signal stream and storing the same occurs in real time compared with the other processing steps.

17. Method of obtaining an evoked potential signal from a variable number of multiple, digitally formatted, pre- and post-stimulation electroencephalographic (EEG) signal streams with an adaptive averaging limit comprising the steps of:

stimulating EEG activity with a plurality of predetermined stimuli;

obtaining a pre-stimulus and a post-stimulus EEG signal stream;

separately averaging said pre-stimulus and post-stimulus EEG signal streams over an increasing K number of sets of pre- and post-stimulation EEG signal streams, wherein each set is defined as an interrelated set of pre- and post-stimulation EEG signal streams having a single time reference present in each set and said time reference being present in all sets;

calculating a time based average noise power $P^-_n$ and $P^+_n$ for said pre-stimulus and a post-stimulus EEG signal streams respectively over a variable K number of sets with the formula:

$$\hat{P}_{\bar{n}} = \frac{1}{TK(K-1)} \sum_{t=1}^{T} \left[ \sum_{k=1}^{K} x_k^2(t) - \frac{1}{K} \sum_{k=1}^{K} x_k(t) \sum_{k=1}^{K} x_k(t) \right]$$

where $x_k(t) = k^{th}$ EEG set,

T = number of data points in each sweep, and $\hat{P}_{\bar{n}}$ = time based pre-stimulus average noise power;

$\hat{P}_{\bar{n}}+$ = time based post-stimulus average noise power calculating a time based average signal power $P^-_s$ and $P^+_s$ for said pre-stimulus and a post-stimulus EEG signal streams respectively over K number of sets with the formula:

$$\hat{P}_s = \frac{1}{T} \sum_{t=1}^{T} \bar{x}_k(t)^2 - \hat{P}_{\bar{n}}$$

calculating a pre- and post-stimulus, estimated, running signal to noise ratio SNR; SNR+ from the respective ratios of the pre- and post-stimulus average signal powers Ps−, Ps+ and average noise powers Pn−, Pn+;

stopping said averaging step when the difference between said pre- and post-stimulus running signal to noise ratios SNR−, SNR+ is less than a predetermined threshold; and identifying an evoked potential signal by comparing said averaged pre-stimulus and post-stimulus EEG signal streams after the cessation of said averaging step and storing the same.

18. Method of obtaining an evoked potential signal from a plurality of digitally formatted, pre- and post-stimulation electroencephalographic (EEG) signal streams comprising the steps of:

stimulating EEG activity with a plurality of timed and grouped stimuli, each stimulus in a group of stimuli having one of substantially the same intensity level or substantially the same frequency, and respective groups of stimuli having increasing levels of intensity or frequency stimuli;

obtaining respective pluralities of pre-stimulus and post-stimulus EEG signal streams during the stimulation step;

filtering said post-stimulus with said pre-stimulus EEG signal streams by separately summing coincidental time based segments of said pre-stimulus EEG signal streams in each group and separately summing said post-stimulus EEG signal streams in each group wherein each interrelated pre- and post-stimulus stream set in all groups includes a time base reference;

forming an array of filtered post-stimulus EEG signal streams with at least two groups wherein the respective time bases of the filtered streams are correlated to each time base reference therein;

filtering said array with a two-dimensional filter; and identifying a plurality of evoked potential signals in the filtered array and storing the same.

19. A method as claimed in claim 18 wherein the array includes filtered EEG signal streams resulting from and representing at least two levels of intensity or frequency stimulation, and the step of filtering said post-stimulus EEG signal streams generates a plurality of first filtered EEG signal streams.

20. A method as claimed in claim 18 wherein the time bases in the first filtered EEG signal streams in said array are aligned.

21. A method as claimed in claim 18 wherein said two-dimensional filter operates in the frequency domain.

22. A method as claimed in claim 18 wherein the step of filtering said array includes the steps of:
transforming said array into a frequency domain using a two-dimensional Fast Fourier Transform;
masking predetermined two-dimensional regions of the transformed array; and
inversely transforming said masked, transformed array with a two-dimensional inverse Fast Fourier Transform.

23. A method as claimed in claim 22 wherein the masking step zero pads predetermined regions in the transformed array in each dimension.

24. A method as claimed in claim 18 wherein the step of stimulating uses one of auditory stimulation, visual stimulation or somato sensory stimulation.

25. A method as claimed in claim 18 wherein the step of identifying a plurality of evoked potential signals in the filtered array and storing the same occurs in real time compared with the other processing steps.

26. A method as claimed in claim 18 wherein an increasing number K of stimuli are used to define each group in the stimulation step and includes the steps of:
calculating a pre- and post-stimulus, estimated, running signal to noise ratios from respective pre- and post-stimulus average signal powers and average noise powers of the pre- and post-EEG signal streams;
stopping the filtering of said post-stimulus EEG signal streams and the stimuli and establishing K for a corresponding group when the difference between said pre- and post-stimulus running signal to noise ratios is less than a predetermined threshold.

* * * * *